United States Patent [19]

Lawton, Jr.

[11] Patent Number: 4,610,158
[45] Date of Patent: Sep. 9, 1986

[54] METHOD FOR DETERMINING THE SEALABILITY OF DRILLING COMPOUNDS

[76] Inventor: Richard Lawton, Jr., P.O. Box 747, Berwick, La. 70342

[21] Appl. No.: 659,777

[22] Filed: Oct. 11, 1984

[51] Int. Cl.[4] .............................................. G01N 15/04
[52] U.S. Cl. ................................................... 73/61.4
[58] Field of Search ......................................... 73/61.4

[56] References Cited

U.S. PATENT DOCUMENTS

| | | | |
|---|---|---|---|
| 2,646,678 | 7/1953 | Standing et al. | 73/61.4 X |
| 2,733,595 | 2/1956 | Twining | 73/61.4 X |
| 3,055,208 | 9/1962 | Gallus | 73/61.4 X |
| 3,172,286 | 3/1965 | Grubb et al. | 73/61.4 |
| 3,289,467 | 12/1966 | Parker et al. | 73/61.4 |
| 4,397,177 | 8/1983 | Cain | 73/61.4 |
| 4,538,452 | 9/1985 | Hrvojic | 73/61.4 |

FOREIGN PATENT DOCUMENTS

| | | | |
|---|---|---|---|
| 617714 | 7/1978 | U.S.S.R. | 73/61.4 |
| 690367 | 10/1979 | U.S.S.R. | 73/61.4 |

*Primary Examiner*—Stewart J. Levy
*Assistant Examiner*—Joseph W. Roskos
*Attorney, Agent, or Firm*—Pravel, Gambrell, Hewitt and Kimball

[57] ABSTRACT

A method for testing drilling compounds, particularly drilling fluids and cements to determine the drilling fluid and cements ability to seal porous formations surrounding the borehole. The method would generally comprise obtaining a representative sample of drilling compound for testing, particular drilling fluid or cement, that has been or will be injected down the borehole and recovered for testing. The sample of fluid is then filtered through a filter press or the like having a porous filter disk with measured size openings that can be closely controlled, or having absolute filtration ability. The sample is then filtered through the disk, usually under pressure, and the rate or the time that the drilling fluid takes to seal a specific size opening in a specific disk is recorded by the number of cubic centimeters of drilling fluids that is recovered until such a seal is established. The test is conducted for a prescribed period of time (30 min.) and the number of cubic centimeters of filtrate recovered is recorded to determine fluids wall cake building ability.

8 Claims, No Drawings

METHOD FOR DETERMINING THE SEALABILITY OF DRILLING COMPOUNDS

BACKGROUND OF THE INVENTION

1. Field of the Invention

The present invention relates to a method for testing drilling compounds, particularly drilling fluids and cements, to determine the drilling compounds ability to seal the porous formations around the borhole.

2. General Background

In the art of drilling oil and gas wells, the borehole of the well is drilled into and through various types of formations, ranging from the granite rock type to very soft and porous earth before making contact with the actual pocket of oil and gas being sought. The industry has developed drilling compounds, in particular drilling fluids and cements which are pumped down into the well hole, as the drilling is ongoing, one of the functions which is to seal the formation around the hole in order to keep the hole free of matter and to have a clean borehole during the drilling process.

The ability of a particular drilling fluid or cement to seal a formation is determined by the percent and size of solids present in the drilling fluid and cement. This is crucial since if a particular drilling fluid is being utilized in an attempt to seal a formation that is very porous, and the particular drilling fluid in question does not contain the necessary percent in size of solids, then the fluid will be unable to seal the formation, and in some cases the entire whole drilling fluid and cement will be lost to the formation until the solids present in the drilling fluid and cement form a seal in the porous formation. This loss of drilling fluid and cement can be a major expense item in the drilling of an oil well, and therefore, it is absolutely crucial that the proper drilling fluid be utilized in order to ensure that when it is put down in the hole that it is not lost and that it seals the formation.

Therefore, prior to the introduction of great amounts of expensive drilling fluid into the borehole, it is crucial that the fluid undergoes a test to ensure that the percent in size of solids in the drilling fluid will be suitable for that particular formation and seal it. At present, there are no tests available which would allow one to determine the size particles and number of particles per a certain volume of drilling fluid. The present methods incorporate the using of a specially hardened filter paper disk to filter drilling fluid. This paper is so constructed that it will filter out colloidal and sub-micron size particles. Therefore, no accurate reading can be made using this particular method.

The following are summaries of U.S. Patents which may be considered to be pertinent art in the field:

U.S. Pat. No. 3,503,933 issued to Whitten, entitled "Formation-Sampling Apparatus", teaches the use of a fluid sampling apparatus to obtain samples of the well bore surface with the apparatus obtaining the sample by being dropped down hole and boring into the borehole wall.

U.S. Pat. No. 3,565,169 issued to Bell, entitled "Formation-Sampling Apparatus", also teaches the use of an improved apparatus for obtaining samples of the wall of a borehole by being dropped down hole and boring into the wall for obtaining the requisite sample to be tested.

U.S. Pat. No. 3,352,361 issued to Urbanosky, entitled "Formation Fluid-Sampling Apparatus", discloses an apparatus having a tubular probe member for movement into sealing engagement with earth formation to obtain samples of formation fluids if any therein. It functions quite like the previous apparatuses.

U.S. Pat. No. 3,011,554 issued to Desbrandes et at, entitled "Apparatus for Investigating Earth Formations", also is a tube dropped down hole for sampling earth formation fluids. A portion of the formation that is being sampled is seal from the drilling fluid until the rest of the sample is obtained.

U.S. Pat. No. 2,829,518 issued to Ruble et al, entitled "Subsurfaces Flow Meter", is also a down hole tube for sampling formation wall and determining fluid flowing from a subsurface formation. It actually measures the rate of a flow of fluids passing through the well bore.

U.S. Pat. No. 3,677,080 issued to Hallmark, entitled "Sidewall Well-Formation Fluid Sampler", relates to an improved formation fluid sampler of the type that is lowered into a well on wire line and directed to sidewall well formation fluid sampler with the ability for obtaining contamination free samples as compared with other samples in the art.

U.S. Pat. No. 3,653,436 issued to Anderson et al, entitled "Formation Sampling Apparatus", is an improved apparatus like that disclosed in the U.S. Pat. No. '933 and U.S. Pat. No. '169 patent for sampling well formations down hole.

U.S. Pat. No. 3,254,531 issued to Briggs, entitled "Formation Fluid Sampling Method", relates to a method a sampling content of earth formations by lowering an apparatus down hole and piercing the earth formation for obtaining requisite sample.

SUMMARY OF THE PRESENT INVENTION

The present invention covers a method for testing drilling compounds, particularly drilling fluids and cements to determine the drilling fluid and cements ability to seal porous formations surrounding the borehole. The method would generally comprise obtaining a representative sample of drilling compound, particular drilling fluid or cement for testing, that will be injected down the borehole. The sample of fluid is then filtered through a filter press or the like having a porous filter disk with measured size openings that can be closely controlled, or having absolute filtration ability. The sample is then filtered through the disk, usually under pressure, and the rate or the time that the drilling fluid takes to seal a specific size opening in a specific disk is recorded by the number of cubic centimeters of drilling fluids that is recovered until such a seal is established. Through this method one is able to determine the relative size of particles in the drilling fluid and whether or not that particular drilling fluid would be adequate in sealing the formation in question, without suffering the loss of the fluid to the formation.

Therefore, it is an object of the present invention to provide a method for filtering drilling fluid on an absolute basis.

It is a further object of the present invention to provide a method of filtering drilling compounds whereby the filtrate has an absolute rated particle size identifiable therein.

It is still a further object of the present invention to provide a method for testing fluids particularly drilling fluids and cements, in order to determine the effectiveness of the fluids ability to seal a porous formation in the borehole, whether they be water base or oil base drilling fluids.

It is still a further object of the present invention to provide a method for testing completion or workover fluids of the like for determining the ability to seal the formation under certain temperatures and pressures as an absolute rating of the filter means.

For a further understanding of the nature and objects of the present invention, reference should be had to the following detailed description, taken in conjunction with the accompanying tables, in which like parts are given like reference numerals and, wherein:

TABLE I is a data sheet of the results of a test series; and

TABLE II is a narrative interpretation of the tests in TABLE I.

DETAILED DESCRIPTION OF THE PREFERRED EMBODIMENT

The preferred embodiment of the method of the present invention is best discussed in light of the present state of the art and the filtration of drilling compounds, particularly drilling fluids and cements under low temperature and high temperature testing. In the present state of the art for testing drilling fluids and cements, the filtration and wall building characteristics of the drilling fluid and cements are determined by means of a filter paper preferably nine (9) centimeters in diameter, utilized in a filter press. Essentially, the filter press apparatus is of the type, presently used by the drilling fluids industry, and generally comprises a cylindrical container for housing a sample of fluid or cement to be tested preferably a three (3) inch diameter cell usually two and a half (2½) inches in height. The chamber has on its upper portion a cap member that can be fitted for providing a means of inducing pressure onto the top of the sample for forcing the sample under pressure through the filtered paper out of the bottom of the chamber through a port and be collected into a graduated cylinder in the like. The chamber is usually sealed by a gasket or the like and supported on a stand. Pressure is usually applied with any non-hazardous fluid medium, either gas or liquid. Presses are equipped with pressure regulators and can be obtained with portable pressure cylinders, or midget pressure cartridges as means for obtaining the requisite pressure. In this particular state of the art, single thickness of the proper nine (9) centimeters filter paper is utilized usually a Whatman No. 50, SF No. 576 or equivalent in the test. During the test, after ensuring that the screen housing the filtered paper is clean and dry, and that the gaskets will properly seal, a sample of mud to be tested is poured into the cell and the assembly is completed. A graduated cylinder is placed under the drain tube to receive a filtrate following the submission of pressure, onto the top of the mud sample, at the end of thirty (30) minutes the volume of filtrate that is filtered through the filter paper is measured. The flow through the pressure regulator is interrupted, and the volume of filtrate is is measured in cubic centimeters. The cell chamber is then disassembled, and the mud is discarded, with using extreme care to save the filter paper with a minimum distrubance to the mud cake layered thereon. The filter cake on the paper is then washed with a general stream of water and a thickness of the filter cake is measured. The thickness of the filter cake is reported in thirty-seconds of an inch in thickness. The steps provided in this particular test is crucial and that it should be understood that in the use of a filter press the paper is so constructed that it will filter out all colloidal and sub-micron size particles and all solid particles allowing only filtrate or fluid to be recovered. Therefore, there is no indication as to what size particles are contained in the mud which may serve as a sealing medium down hole.

In the preferred embodiment of the present invention, the steps provided in the filtration method as is noted in the present state of the art are followed, except for the fact that the filter means provides an absolute filtration means i.e., a screen or the like which has a absolute sized pore to which the mud is filtered under pressure. This aspect of the method of testing is crucial and novel in that upon pressurizing the vessel and the mud sample being filtered through the absolute rated filter means, the measured size openings allow only particles which are smaller than that particular opening to filter therethrough, and one can determine the rate under which the filter disk is sealed by the flow of mud therethrough. This rate of seal is recorded by the number of cubic centimeters of drilling fluid that is recovered until a seal is established on the porous filter disk.

Therefore, in the process of the present invention, rather than utilizing a filter paper which filters all particles and allows only complete filtrate through, the process of the present invention utilizes a filter means whereby only those particles which are smaller than the absolute rated openings in the filter means filter therethrough, and therefore, when a seal is established on the surface on the filter porous disk, one can establish the time involved in sealing such a porous area, and therefore, will have a clear indication of whether or not that particular mud or drilling fluid will accomplish the proper sealing of the formation, or whether the sealing rate is so slow that valuable cement or fluids are being lost into the formation. Following that determination, the particle size of drilling fluid can be adjusted so that larger particles are included therein so that proper sealing can take place without significant loss of the drilling fluid.

Such a porous filter disk having an absolute rating would also be utilized with the methods involving high pressure and high temperature testing. As is understood, often times down hole there are tremendous pressures and temperatures which the drilling fluid is subjected to, and it is imperative that under testing conditions these pressures and temperatures be closely followed so that one can determine whether or not the drilling fluid or mud being utilized down hole is in any way altered by the pressures or temperatures involved. Therefore, the seal rate method would also include subjecting the mud sample to a very high temperature by placing the container in a jacket, and subjecting the mud to a very high pressure and by creating a differential pressures on the sample allowing the sample to filter through the medium, and the results are obtained in precisely the same way as in the low temperature, low pressure, testing method.

What follows are examples of the manner in which a borehole being drilled may be vastly improved if it is determined before hand, through the novel testing method using the absolute filter "seal rate" method of the present invention, what the rate of seal on that particular drilling compound being used in the well is. The seal rate is the proper seal rate for the particular formation, then the well in question will be drilled more efficiently, and of course with less expense.

EXAMPLE 1

In a producing well, a 9 and 5/18 casing was set at 12,000 feet. While drilling with a 16.5 pounds per gallon water base drilling fluid with a seal rate of 11.6 cc (as had been previously measured by the present invention method of testing), no problems were encountered. Rig procedures were changed while drilling at 13,700 feet a total loss of circulation of the mud was encountered. The seal rate on the drilling fluid had changed from 11.6 cc to 22.0 cc. Cement was spotted in the borehole to regain circulation. It was learned that while drilling cement that loss of circulation occurred in a sand bed at 12,600 feet that was drilled within 11.6 cc seal rate. When the seal rate was allowed to increase to 22.0 cc, the drilling fluid no longer was able to seal the sand and loss of circulation was encountered.

EXAMPLE 2

On this same hole, a 7 and ⅝ inch liner was set at 14,000 feet. The water base drilling fluid was displaced by a 17.7 p.p.g. inverted emulsion oil base mud with a seal rate of 7.2 cc. While drilling at 15,500 feet, the borehole began to lose fluid the seal rate at this time was 17.4 cc cement was spotted and circulation was regained. At this time the oil base mud was displaced with water base mud. The hole was drilled to a total depth of 18,700 feet with no problems being encountered and the seal rate have being maintained below 10.0 cc and the seal rate being 7.6 cc.

EXAMPLE 3

This example was no previous testing under the method of the present invention, for the seal rate of the mud in question. The results are as follows. The first hole was drilled off the platform to below intermediate casing depth with a 16.9 p.p.g. mud with a seal rate of 22.2 cc. The drill string was differentially stuck at 13,500. The hole was plugged back to 12,000 feet where the hole was sidetracked. The hole was then drilled back to 13,500 feet where the drill string was stuck again, the seal rate at this time was 19.4 cc the hole was again plugged back to 12,000 feet and again sidetracked. The hole was drilled to 15,000 feet with no trouble with the seal rate of 9.6 cc. The total days loss to sidetracking was 84 days. The total cost of the hole was $8 million when the hole should have cost $2.5 million.

EXAMPLE 4

This example, an oil company sent the mud in for the seal rate test under the present invention. The mud was at 17.8 pounds per gallon with a seal rate of 19.2 centimeters. The oil company was informed that this mud had the ability to stick drill string. Twenty-four (24) hours later a sand bed was drilled and the drill string was stuck. The hole had to be sidetracked with very expensive oil base mud. Had the mud been treated to lower the seal rate this would not have occurred.

As is apparent from the following examples, the seal rate test determining the amount of cubic centimeters of mud sealing the porous filter within a certain given time, is an accurate way of determining the sealability of the drilling compound down a particular formation. This test, totally novel in the industry, allows a company prior to utilizing the expensive mud to having it tested through the present invention, and have a predetermination as to whether or not the mud has enough solids in it in order to seal the formation properly during the drilling process.

As a further example of the process of the present invention, Tables I and II are representative of the type data that is received as the result of the test. As seen in Table I, the process which is undertaken would comprise taking a particular sample of drilling fluid or the like, and subjecting it in the container to a pressure of 500 pounds per square inch, with the porous disc utilized having a number of 15 disc i.e., a 150 mesh disc. The drilling compound upon being poured into the filter unit would, because of the porousness of the disc, flow through the disc rather easily, and thus, until the drilling compound would begin to form a layer on the disc and form a seal, the cubic centimeters of fluid prior to the seal would be measured at 31.4 centimeters as the Seal Rate Fluid loss, as seen in column 3 of Table I. Following the formation of the cake, a second fluid loss would be measured which would be the Seal Rate Filtrate indicated in column 4, which would be a filtrate filtering through the cake. In this case it would total 49 cubic centimeters, until the cake is completely sealed off. The second run of the test, which shows a 20 mesh disc, the seal rate fluid loss would be 14.2 cc and the seal rate filtrate would be 47 cc. This particular test shows that the number of cc in the seal rate fluid loss and the seal rate filtrate were too high, and this particular compound would not do the proper sealing of the foundation. Therefore, as seen further in the columns, a combination of Poly Gel, Stabil-Trol, and Starlose, which are products such as asphalt or the like, utilized to increase the compound, provided a 18 cc, 10.2 cc, and 8.8 cc Seal Rate Fluid loss respectively, and a 44 cc, 32 cc, and 15 cc Seal Rate Filtrate respectively. The ideal seal rate fluid loss is contained in the column whereby the number of cc in the Seal Rate Fluid loss was 8.8 cc and the seal rate filtrate was 15 cc. With this type of fluid loss and filtrate amounts, it is determined that the compound properly sealed within a short amount of time and would reflect a rather thin layer of compound yet compact enough to seal. This would be ideal for the situation downhole in view of the fact that the compound must seal, yet it is not necessary that the compound form a thickened cake in view of the fact that that they may cause sticking of the drill string.

Table II reflects the conclusion that can be drawn from looking at the test results, which show that the seal rate of the compound prior to the addition of these compounds indicates that the compound shows the ability to stick the pipe in highly permable sands with low differential pressures. One would expect the hole to lose excessive amount of compound while drilling and on trips. This is indicated in view of the fact that the Seal Rate Fluid loss at 31.4 cc is very high, therefore, there is a great fluid loss prior to the sealing of the compounds. A Seal Rate Filtrate of 49 cc would indicate there would be excessive wall cake build up in order to effect sealing. If 49 cc of filtrate is filtered through prior to the seal being effected, then it would take a rather thickened cake of compounds in order to effect a seal. Such a thickened cake would cause balling or trouble with inlogging. Likewise, with the seal rate on a number 20 disc, the compounds would show the ability to seal where sand beds have less permability, but the compounds still show excessive wall cake build up, due to the high rate of filtrate, i.e., 47 cc. Therefore, from the overall determination as seen in Table II, one could expect high penetration rates and very poor suspension properties due to the low percent of colloidal solids. This, again is, of course, prior to the addition of the compounds as shown in the lab test. Upon the compounds being added, one would then have the ability to have effectuated a proper seal in the compound sealing function.

Because many varying and different embodiments may be made within the scope of the inventive concept herein taught, and because many modifications may be made in the embodiments wherein detailed in accordance with the descriptive requirement of the law, it is to be understood that the details herein are to be interpreted as illustrative and not in a limiting sense.

TABLE I

DATA SHEET

| Pressure | Disc Size | Seal Rate* Fluid Loss | Seal Rate Filtrate | API Filtrate | +74 u |
|---|---|---|---|---|---|
| 500 psi | #15 | 31.4 cc | 49 cc | +48 cc | 0.90% |
| 500 psi | #20 | 14.2 cc | 47 cc | — | — |
| | | *Whole Mud Lab Test | | | |
| Product | | 500 psi | 500 psi | 100 psi | |
| 10#/bbl Poly Gel | #15 | 18.0 cc | 44 cc | — | — |
| 10#/bbl Stabil-Trol | #15 | 10.2 cc | 32 cc | — | — |
| 8#/bbl Starlose | #15 | 8.8 cc | 15 cc | 19.8 cc | 4.5% |
| Sheared for 2 hrs. | #15 | 9.6 cc | 10.2 cc | 14.4 cc | 3.0% |

TABLE II

COMMENTS:

A. Seal Rate on #15 disc.
  1. Mud shows ability to stick pipe in highly permeable sands with low differential pressures.
  2. Expect hole to lose excessive amount of mud while drilling and on trips.
B. Seal Rate Filtrate on #15 disc.
  1. Mud shows excessive wall cake buildup.
    a. May have trouble logging.
    b. Stabilizers will ball up if large sand beds are encountered.
C. Seal Rate on #20 disc.
  1. Mud shows ability to seal where sand beds have less permeability.
  2. Mud still shows excessive wall cake build up.
D. Mud shows low percent of colloidal solids.
  1. Expect high penetration rates.
  2. Very poor suspension properties due to low percent of colloidal solids.

SUMMARY: The particle size distribution in this mud needs to be adjusted on both ends to improve suspension, Seal Rate Fluid Loss, and Seal Rate Filtrate. This can be accomplished with various materials with very little effect on penetration rates and overall well cost.

What is claimed as invention is:

1. A method for for determining particle size distribution in drilling compounds, particularly drilling fluids and cements, in order to determine the drilling fluids and cements ability to seal porous formations, comprising the following steps:
  a. providing a measured portion of drilling compound that has been or will be circulated down hole;
  b. providing filter means having consistent measured openings therethrough;
  c. filtering said drilling compound through said filter means under a given pressure;
  d. effecting a drilling compound layered seal on said filter means;
  e. filtering additional drilling compound through the filter means under increased pressure over a certain length of time;
  f. measuring the amount of filtrate recovered; and
  g. determining the rate of formation of said seal as the function of the amount of filtrate recovered.

2. The method in claim 1, wherein said filter means is contained in a filter press apparatus.

3. The method in claim 1, wherein said filtering means comprises preferable a metalic screen having absolute-rated openings over its entire surface.

4. The method in claim 1, wherein the greater formation of said seal on said filter means determines the ability of the drilling fluid to seal the particular porous formation.

5. The method in claim 1, further comprising the step of adding additional solids to said drilling fluid if said rate of seal indicates excessive loss of fluid therethrough.

6. A method for for determining particle size distribution in drilling compounds, particularly fluids and cements, for determining the compounds ability to seal porous formations downhole, comprising the following steps:
  a. providing a portion of drilling compound that will be or has been circulated down hole;
  b. providing filter means, having consistent measured openings therethrough, further comprising:
    i. an absolute rated filter disk through which said fluid is filtered therethrough;
    ii. a container portion housing said filter disk;
  c. pouring a measured amount of said drilling fluid into said container for filtering a portion through said filter disk;
  d. subjecting said portion of drilling fluid to predetermined temperature and pressure;
  e. filtering said drilling fluid through said filter disk under a predetermined temperature and pressure;
  f. effecting a drilling compound layered seal on said filter disk interrupting the flow of filter drilling fluid herethrough;
  g. measuring the amount of filtrate that is filtered through said filter disk upon that seal being effected; and
  h. determining the rate of seal as a function of the amount of filtrate covered, wherein the rate of seal effected determines the sized particles in said drilling fluid, and further determines the ability of fluid to seal the formation.

7. The process in claims 1 or 6, wherein following the obtaining of a sample of filtrate, the amount of filtrate is recorded to obtain an indication of wall cake build-up.

8. The process in claims 1 or 6, wherein the build-up of wall cake further informs what chemical or mechanical treatment is needed to control the particle size distribution in the drilling fluid.

* * * * *